United States Patent
Wissel et al.

(10) Patent No.: US 11,426,240 B2
(45) Date of Patent: Aug. 30, 2022

(54) STRESS PREDICTION AND STRESS ASSESSMENT FOR DEVICE INSERTION INTO A DEFORMABLE OBJECT

(71) Applicant: KONINKLIJKE PHILIPS N.V., Eindhoven (NL)

(72) Inventors: Tobias Wissel, Lübeck (DE); Hernán Guillermo Morales Varela, Suresnes (FR); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 698 days.

(21) Appl. No.: 16/468,303

(22) PCT Filed: Dec. 6, 2017

(86) PCT No.: PCT/EP2017/081598
§ 371 (c)(1),
(2) Date: Jun. 11, 2019

(87) PCT Pub. No.: WO2018/108640
PCT Pub. Date: Jun. 21, 2018

(65) Prior Publication Data
US 2021/0298829 A1    Sep. 30, 2021

(30) Foreign Application Priority Data

Dec. 13, 2016   (EP) .................................... 16306676

(51) Int. Cl.
*A61B 34/10* (2016.01)
*G06T 7/11* (2017.01)
(Continued)

(52) U.S. Cl.
CPC .............. *A61B 34/10* (2016.02); *G06F 30/23* (2020.01); *G06T 7/0016* (2013.01); *G06T 7/11* (2017.01);
(Continued)

(58) Field of Classification Search
CPC .............. A61B 34/10; A61B 2034/102; A61B 2034/105; G06F 30/23; G06T 2200/04;
(Continued)

(56) References Cited

FOREIGN PATENT DOCUMENTS

JP        2014200549 A      10/2014

OTHER PUBLICATIONS

Gijsen F. et al., "Simulation of stent deployment in a realistic human coronary artery" biomedical engineering online (Year: 2008).*
(Continued)

*Primary Examiner* — Manuchehr Rahmjoo

(57) ABSTRACT

A stress prediction device for predicting mechanical stress exerted to a deformable object due contact between the object and an external device that is to be inserted into the object at an intended insertion position comprises a segmentation unit configured to access generic model data representing a generic reference object that comprises predefined secondary landmark features at predefined landmark positions, which are not identifiable using a predefined imaging technique, and pre-insertion object image data acquired using the imaging technique. It provides segmented object model data which comprises associated mapped landmark position data indicative of mapped landmark positions of the secondary landmark features. A stress determination unit determines and provides predictive stress information indicative of mechanical stress exerted to at least one of the secondary landmark features at the associated mapped landmark position due to mechanical contact between the object and the external device.

14 Claims, 5 Drawing Sheets

(51) Int. Cl.
| | |
|---|---|
| *G06T 7/73* | (2017.01) |
| *G16H 50/50* | (2018.01) |
| *G16H 30/20* | (2018.01) |
| *G16H 50/30* | (2018.01) |
| *G16H 30/40* | (2018.01) |
| *G06F 30/23* | (2020.01) |
| *G06T 7/00* | (2017.01) |
| *G16H 50/20* | (2018.01) |

(52) U.S. Cl.
CPC ............... *G06T 7/75* (2017.01); *G16H 30/20* (2018.01); *G16H 30/40* (2018.01); *G16H 50/30* (2018.01); *G16H 50/50* (2018.01); *A61B 2034/102* (2016.02); *A61B 2034/105* (2016.02); *G06T 2200/04* (2013.01); *G06T 2207/10081* (2013.01); *G06T 2207/30048* (2013.01); *G06T 2207/30052* (2013.01); *G16H 50/20* (2018.01)

(58) Field of Classification Search
CPC . G06T 2207/10081; G06T 2207/20124; G06T 2207/30048; G06T 2207/30052; G06T 2207/30101; G06T 7/0012; G06T 7/0016; G06T 7/11; G06T 7/149; G06T 7/75; G16H 20/40; G16H 30/20; G16H 30/40; G16H 40/63; G16H 50/20; G16H 50/30; G16H 50/50
See application file for complete search history.

(56) References Cited

OTHER PUBLICATIONS

International Search Report and Written Opinion, International Application No. PCT/EP2017/081598, dated Jan. 31, 2018.
Gijsen, F. et al., "Simulation of stent deployment in a realistic human coronary artery", BioMedical Engineering OnLine, Aug. 2008.
Wang, V. et al., "Unsupervised segmentation and personalised FE modelling of in vivo human myocardial mechanics based on an MRI atlas", IEEE, 2012.
Neragi-Miandoab, S, Michler, RE (2013). A review of most relevant complications of transcatheter aortic valve implantation. ISRN Cardiol, 2013:956252.
Erkapic, D, De Rosa, S, Kelava, A, Lehmann, R, Fichtlscherer, S, Hohnloser, SH (2012). Risk for permanent pacemaker after transcatheter aortic valve implantation: a comprehensive analysis of the literature. J Cardiovasc Electrophysiol, 23, 4:391-7.
Saremi, F, Abolhoda, A, Ashikyan, O, Milliken, JC, Narula, J, Gurudevan, SV, Kaushal, K, Raney, A (2008). Arterial supply to sinuatrial and atrioventricular nodes: imaging with multidetector CT. Radiology, 246, 1:99-107; discussion 108-9.
Hein-Rothweiler, R. et al., "Aortic Annulus to Left Coronary Distance as a Predictor for Persistent Left Bundle Branch Block After TAVI", Catheterization and Cardiovascular Interventions 00:00-00 (2016).
Hamdan, A. et al., "Inverse Relationship Between Membranous Septal Length and the Risk of Atrioventricular Block in Patients Undergoing Transcatheter Aortic Valve Implantation", JACC: Cardiovascular Interventions, 2015.

* cited by examiner

STRESS PREDICTION AND STRESS ASSESSMENT FOR DEVICE INSERTION INTO A DEFORMABLE OBJECT

CROSS-REFERENCE TO PRIOR APPLICATIONS

This application is the U.S. National Phase application under 35 U.S.C. § 371 of International Application No. PCT/EP2017/081598, filed on 6 Dec. 2017, which claims the benefit of European Patent Application No. 16306676.4, filed on 13 Dec. 2016. These applications are hereby incorporated by reference herein.

FIELD OF THE INVENTION

The present invention relates to a stress prediction device for predicting mechanical stress expected from a mechanical contact interaction between a deformable object and an external device to be inserted into the object at a given insertion position, to a method for assessing mechanical stress and to a computer program.

BACKGROUND OF THE INVENTION

Minimally invasive interventions involving the insertion of a medical device into an object such as the heart of a living being bear a risk of traumatic destruction of functional tissue. For that reason, imaging techniques have been employed in order to allow determining the position of the medical device even during an intervention. However, not all kinds of tissue can be made visible in standard imaging techniques.

JP2014200549A is concerned with preventing occurrence of complications associated with the execution of transcatheter aortic valve replacement (TAVR), which is also referred to as transcatheter aortic valve implantation (TAVI) herein. The document describes a medical image processing apparatus that includes a region extraction unit that extracts sub-regions of the heart like a ventricle and an atrium of a heart from first medical image data showing contrast features of a heart region of a subject; a peripheral tissue detection unit that detects regions of peripheral tissues existing around an aortic valve in the first medical image data on the basis of a database determining a positional relation of elements in the heart region and the regions extracted by the extraction unit; an image generation unit that generates second medical image data showing the peripheral tissue regions detected by the peripheral tissue detection unit; and an output unit that outputs the second medical image data.

SUMMARY OF THE INVENTION

It is an object of the present invention to provide assistance for further reducing the risk of complications in the context of an insertion of an external device into an object such as an organ of the human body.

According to a first aspect of the present invention, a stress prediction device is provided for predicting mechanical stress exerted to a deformable object due to mechanical contact between the object and an external device that is to be inserted into the object and to be positioned at a pre-determined intended insertion position. The stress prediction device comprises:

a segmentation unit, which is configured to access generic model data, which represents a three-dimensional generic reference object comprising pre-defined secondary landmark features at predefined landmark positions, which are not identifiable using a predefined imaging technique, and which comprises spatially resolved mechanical reference data representing at least one mechanical property of the generic reference object, and to access pre-insertion object image data acquired using the imaging technique and representing a three-dimensional image of the object prior to insertion of the external device;

using the pre-insertion object image data and the generic model data, to provide segmented object model data which represents the object and its spatially resolved mechanical property and comprises associated mapped landmark position data indicative of mapped landmark positions of the secondary landmark features within the object; and comprising:

a stress determination unit, which is configured to receive insertion position data indicative of the pre-determined intended insertion position, and device model data, which represents the external device, and to calculate and provide, using the segmented object model data, the device model data and the intended insertion position data, predictive stress information indicative of mechanical stress exerted to at least one of the secondary landmark features at the associated mapped landmark position due to mechanical contact between the object and the external device when inserted into the object at the intended insertion position.

The stress prediction device of the first aspect of the invention allows predicting the mechanical stress expected from the mechanical contact interaction between a deformable object and a device that is to be inserted into the object and to be placed at a pre-determined intended insertion position. It is particularly advantageous that the stress prediction device allows predicting stress caused by the insertion even for certain features of the object, herein called the secondary landmark features, which cannot be distinguished in object image data provided as an input to the stress prediction device. Such secondary landmark features are known and included in the generic model data representing a three-dimensional generic reference object. Since there are anatomical variations across subjects, the present invention allows achieving a high likelihood of identifying a critical region at a specific position of the secondary landmark features in the absence of their direct visibility in the object image data.

The achieved stress prediction for such "invisible" features of the object under investigation forms a basis for making an assessment of a suitability of an intended (planned) insertion position and thus helps avoiding undesired damage to the stress-sensitive features of the object under investigation during or after the insertion of a permanently implanted device. The stress prediction device thus forms a very helpful tool of assistance in planning an insertion position of a device into a deformable object. The stress-prediction device is particularly useful in medical and biological application cases, such as predicting stress on certain functional landmarks in sections of an organ due to an insertion of a device into the organ. However, its applicability also extends to non-medical and non-biological application cases.

Mechanical stress at a given position of the deformable object under investigation is understood herein as a physical quantity that is indicative of a mechanical force according to mechanical physics, which is exerted at the given position. An insertion of a device into the deformable object may provide such mechanical force and have effects to a landmark feature, such as a displacement from its original position assumed in absence of the force, compression, tension, shear, bending, or torsion. Any of these different effects represents mechanical stress and can be quantified by an appropriate measure for determining the mechanical stress that the device inserted into the object may cause on the object.

For predicting mechanical stress, generic model data is used that represents a three-dimensional generic reference object of the same object type as the deformable object. A generic reference object is an object of a given object type that has typical object features common to a statistically significant majority of objects belonging to that object type. The generic reference object (herein in short: reference object) comprises predefined landmark features that have respective associated predefined spatial landmark positions within the reference object. The spatial landmark position may refer to a point within the reference object or to a one-dimensional, two-dimensional or three-dimensional section of limited extension within the reference object, which section covers at least a fraction of the landmark feature.

In particular, in accordance with the present invention, the generic reference object comprises predefined secondary landmark features. The secondary landmark features differ from other landmark features, which herein are referred to as primary landmark features, in that they cannot be visualized using the given imaging technique. Thus, what forms a secondary landmark feature or a primary landmark feature may depend on a given imaging technique used for obtaining the object image data of the deformable object under investigation, which object image data is used for stress prediction according to the present invention.

Furthermore, the generic reference object comprises spatially resolved mechanical reference data indicative of at least one physical quantity representing at least one mechanical property of the generic reference object. In the context of the present disclosure, the mechanical property can also be called a mechanical deformation property of the generic reference object. An exemplary and non-exhaustive list of mechanical properties of the generic reference object is given by quantities such as elasticity, flexibility, resilience, compressive strength, hardness, plasticity and ductility.

In the stress prediction device of the present invention, the object image data that represents a three-dimensional image of the object, undergoes a model-based segmentation. The model is provided in the form of generic model data and represents a reference object that comprises predefined secondary landmark features at predefined landmark positions, which are not identifiable using the predefined imaging technique. The segmented object model data provided by the segmentation unit thus includes associated mapped landmark position data indicative of mapped landmark positions of the secondary landmark features within the object. These secondary landmark features are not identifiable using the imaging technique.

Therefore, even though the secondary landmark features of the generic model data does not "show" in the object image data, their expected positions are determined as the mapped landmark positions, and a stress amount at their expected positions in the object under investigation can now be determined, by making use of the segmented object model data which represents the object and its spatially resolved mechanical property. The mechanical stress prediction thus also bases on including the spatially resolved mechanical property in the segmentation process.

The mapped landmark positions of the secondary landmark features are then used by the stress determination unit to calculate mechanical stress in the object (in particular at positions close to the mapped landmark positions), as expected from the mechanical interaction due to the contact between the object and the external device to be inserted into the object at the pre-determined intended insertion position. In order to calculate the mechanical stress, the stress determination unit additionally receives the insertion position data and device model data.

The segmented object model data comprises information pertaining to the geometry of the object, to the position of the secondary landmark features (in the form of the mapped landmark positions) and to the at least one mechanical property of the object (for instance in the form of spatially resolved mechanical data). The device model data comprises information pertaining to the geometry of the device to be inserted into the object and to at least one physical quantity representing the at least one mechanical property of this external device. This mechanical property can be represented by one or more quantities from the same set of quantities related to deformability as mentioned above.

The stress determination unit is configured to calculate mechanical stress at least at the mapped landmark positions caused by the external device having a known device geometry and known mechanical properties. It is also configured to provide, that is to output, predictive stress information, which is indicative of mechanical stress exerted to at least one of the secondary landmark features at the associated mapped landmark position due to mechanical contact between the object and the external device when inserted into the object at the intended insertion position.

The stress information data provides assistance for further reducing the risk of complications in the context of an insertion of the external device into the object by a priori predicting the mechanical stress expected by a hypothetical insertion of the external device into the object at the given insertion point.

In the following, embodiments of the first aspect of the present invention will be described.

The following description distinguishes between pre-insertion object image data and post-insertion object image data. The former can be used in the context of stress prediction, while the latter and the former together can be used to perform stress assessment after insertion. Generally, the term "pre-insertion" refers to a time or state prior to insertion of the device into the object, and the term "post-insertion" refers to a time or state after insertion of the device into the object.

In some embodiments, the object image data, pre-insertion and/or post-insertion, is computed tomography (CT) data acquired by a computed tomography imaging technique. A CT scan makes use of computer-processed combinations of a plurality of X-ray images that are taken from different angles to produce cross-sectional (tomographic) images (virtual "slices") of specific areas of an imaged object.

In some of these embodiments, the generic model data represents a three-dimensional generic reference heart and the pre-insertion object image data is heart image data acquired from a heart of a living being. The generic reference heart is in some cases a model heart statistically based on a ground truth population of hearts. A geometry of the generic reference heart and landmark positions of the secondary landmark features and the spatially resolved mechanical reference data can be determined by a statistical determination rule based on a plurality of hearts belonging to the population. Ground truth refers in the sense of this invention to data provided by direct observation as opposed to data provided by inference. The generic reference object comprises in some cases a multicompartment triangulated mesh of vertices connected into triangles. The secondary landmark features can for instance be defined as detailed subsets of mesh vertices or mesh triangles defining the generic reference object. They can alternatively be defined in relation to such mesh vertices or triangles in the generic reference object (as a relative mesh).

Encoding of the secondary landmark features within the generic model data can be accomplished based on alternative imaging techniques which allow the identification of the secondary landmarks but are different from the imaging technique used for acquiring the pre-insertion object image data. In other cases, and for specific objects such as hearts and specific sets of secondary landmarks, other approaches are used, that are not directly related to an imaging technique. In the particular case of the atrioventricular (AV) node block of the human heart, a localization of these conduction system landmarks can be obtained via electrophysiological (EP) catheter application pre-treatment for subsequent encoding in the generic model data of a generic reference heart.

In the segmentation process, the "invisible" secondary landmarks are passively adapted to the object image data by making use of a mix of spatial transformations or deformations of neighboring primary landmarks/mesh parts in each iteration of the optimization. Suitable spatial transformations and deformations are known as such. For instance, steps of estimating a global rigid transformation, estimating a global affine transformation, estimating a multi-compartment affine transformation and finally estimating nonrigid deformations can be performed. All of these steps are optimizations of a cost energy function, which, roughly speaking, forms a sum of an external image energy and an internal energy of the model. External image energy can for instance be defined in terms of an attraction to image contrast features of certain parts of the model, e.g., a typical appearance of a heart septum in CT imaging data. Internal energy associated with the model is for instance defined in terms of its stiffness or its desire to stick to a statistical mean shape. The optimization is solved iteratively using first or secondary order unconstrained optimization.

The simplest case is where the secondary landmarks define details in the form of subsets of mesh data defining a mesh of vertices or triangles and comprised by generic model data.

In different embodiments, different types of external devices can be used. Other embodiments allow a device type selection from a set comprising different predetermined device model data representing different device, and in some variants also are configured to allow user input for effecting a device sizing prior to stress determination. An example of an external device that is typically inserted into the heart of a living being is a stent. A stent can be defined as a tube that is configured to be inserted into a lumen of an anatomic vessel or duct. Some stents are configured to increase their radius once inserted inside the vessel. The insertion of a stent into a suitable section of the heart may generate stress in dependence on the geometry of the stent and the heart and on its respective mechanical characteristics.

In some of these embodiments, the device model data represents comprises a balloon-inflatable stent as the external device. In these embodiments, the stress determination unit is configured to calculate the mechanical stress at the mapped positions using a predetermined balloon force value indicative of a radial force applied by the balloon-inflatable stent in an inflated state to radially surrounding tissue at the insertion position. The geometry of the inflated state is variable and depends on the geometry of the stent and on the object at the insertion position, as well as on their respective mechanical characteristics. This means that the same stent may present different inflated states in dependence on the object into which is inserted or on the insertion position within a given object. The extended state of the stent does not necessarily represent the fully extended stent as which mainly depends on its geometry and mechanical properties. It may comprise intermediate extensions between a pre-insertion extension of the stent and the extension of the fully extended stent.

In other embodiments, the device model data represents a self-expandable stent as the external device. In these embodiments, the stress determination unit is configured to calculate the mechanical stress at the mapped positions using a predetermined expansion force value indicative of a radial force applied by the self-expandable stent in an expanded state to radially surrounding tissue at the insertion position. Here again, the expanded state does not necessarily represent the fully extended stent. In some of these embodiments the predetermined balloon force values or the expansion force values are given in the form of a force curve relating the magnitude of the balloon force or the expansion force to a respective position at the stent.

The stents, regardless of their type, may in some embodiments comprise a pericardial valve which is attached to the stent.

In preferred embodiments, the stress determination unit is configured to calculate the mechanical stress using a finite element method, in particular in the form of a simulation of the object in the post-insertion state. The finite element method (FEM) is a numerical technique that is used for finding approximate solutions to boundary value problems by dividing a whole domain or an object under study into smaller, simpler parts that are called finite elements. The simple equations that model these finite elements are then assembled into a larger system of equations that models the whole domain or the object under study. FEM then uses variational methods from the calculus of variations to approximate a solution by minimizing an associated error function. In some embodiments, in particular those which involve a simulation of the object in the post-insertion state, the stress determination unit is configured to calculate the mechanical stress at the mapped positions using the finite element method using the object model data which comprise mesh data defining a three-dimensional model of the object.

Boundary conditions, which are typically used to determine the stress in TAVI applications using the FEM simulation, include for instance a pre-insertion state with an equilibrium between blood pressure and an internal energy of surrounding tissue walls of the insertion position, such as the aortic root. For balloon-expandable TAVI devices an additional boundary condition is a post-insertion state, in which an external force is applied by the balloon onto the surface of the stent, and therefore, via the contact to the tissue, a force on the aorta. For self-expandable devices a certain internal elastic energy is stored within the crimped stent, which is then released during deployment and leads to a corresponding force as described above. Typically, manufacturers have curves from device testing, which provide information about this expansion. Further constraints to the FEM simulation are the mechanical properties of the device and of the tissue.

In some embodiments, the generic model data represents a three-dimensional generic reference object spatially segmented into different distinguishable object segments according to a predefined segmentation scheme that includes primary landmark features associated with pre-determined primary landmark positions and identifiable in the object image data using the predefined imaging technique. In these embodiments, the segmentation unit is preferably configured to determine the mapped landmark positions using the primary landmark positions.

By using the computed tomography imaging technique on a heart of a living being, several anatomical regions can be identified from the resulting object image data. In some embodiments of the present stress prediction device, the primary landmark features comprise a plurality of anatomical regions that are enclosed by a multi-compartment triangulated mesh. The anatomical regions are in some cases the left and right ventricles, the left and right atria, the myocardium surrounding the left ventricle and the trunks of the aorta, the pulmonary artery and the pulmonary veins.

On the other hand, also with reference to using the computed tomography imaging technique on the heart of the living being, there are other structures that cannot be identified on the resulting object image data because they do not generate contrast features on the heart image data. Examples of these structures, which are referred to as the secondary landmark features herein, are those structures belonging to the conductive system of the heart. In some embodiments, the secondary landmark features comprise at least one part of a heart-conductive system of the generic reference heart including at least one of an atrioventricular (AV) node, a His bundle and a fraction of the left or right bundle branch, which are not identifiable in the heart of the living being using the computed tomography imaging technique. The stress prediction device of the present invention allows making stress predictions even for these "invisible" secondary landmark features.

In some embodiments, the stress prediction device comprises additional post-insertion stress assessment capability. In these embodiments, the segmentation unit is additionally configured to receive post-insertion object image data acquired, using the imaging technique, from the three-dimensional object with the external device positioned at a given current insertion position;

using either the post-insertion object image data and the segmented pre-insertion object model data or the post-insertion object image data and the generic model data, to provide insertion position data indicative of a current insertion position of the external device, and segmented post-insertion object model data which comprises associated mapped post-insertion landmark position data indicative of mapped post-insertion positions of the secondary landmark features within the object in the post-insertion state and wherein the stress determination unit is additionally configured to calculate and provide, using the insertion position data, the segmented pre-insertion object model data and the segmented post-insertion object model data, post-insertion stress information indicative of mechanical post-insertion stress exerted to at least one the second landmark features by the mechanical contact between the object and the external device inserted into the object at the current insertion position.

The stress assessment capability allows an additional assessment of the mechanical stress on the object created by inserting the device once the device has been inserted into the object at the current insertion position. In order to perform this task, the segmentation unit is additionally configured to receive post-insertion object image data acquired, using the imaging technique, from the three-dimensional object with the external device positioned at the current insertion position. Furthermore, it is configured to provide segmented post-insertion object model data which represents the three-dimensional object in a post-insertion state with the external device in the current insertion and its spatially resolved mechanical property. This is performed by using the post-insertion object image data. As an illustrative example, pre-insertion object image data which has been segmented using the generic object model data allows determining segmented pre-insertion object model data representing a deformed mesh topology consisting of vertices that are linked to certain locations of at the object. Post-insertion object image data is provided and segmented using a possibly adapted deformable model of the object, which has, however, the same topology.

Both object models, pre- and post insertion, have naturally defined correspondences via an identical mesh topology. By registration, which given these correspondences can for instance be done in a least-squares fashion (average across all vertices), both object models are in the same coordinate system, where displacement data then can be estimated. The displacement data is data pertaining to a mesh deformation before and after the insertion of the device.

Post-insertion stress information determined using the post-insertion object image data is in some embodiments used to improve the predictive stress information that is calculated without making use of the post-insertion object image data. A comparison of the pre-insertion and post-insertion object image data allows determining feedback that can be used to improve the accuracy of the predicted mechanical stress performed using only the segmented object model data and the device model data, and is thus used in some embodiments of the second aspect to refine the calculation of the predictive stress information. More specifically, this advantage of the additional post-insertion stress assessment capability of the stress prediction device is that the mechanical properties of the object as well as boundary conditions such as those mentioned above can be refined in a patient-specific or even in a general manner using the post-insertion image data. The post-insertion state corresponds to a second equilibrium state, including the possibly not fully deployed, but nevertheless inserted device. This refinement is similar to a feedback loop that allows tuning the aforementioned parameters, conditions and constraints. It starts at the pre-operative state and arrives at the post-treatment state with the given insertion and displacements observable in the post-insertion object image data.

Useful information for the improvement of stress prediction for future cases can also be achieved using the determined post-insertion stress information in a given case if only post-insertion image data is available.

However, the stress assessment capability, that is, a determination of post-insertion stress information described in the foregoing sections can also be used alone, without making use of stress prediction. This is described in the following as a second aspect of the present invention.

According to a second aspect of the present invention, thus, a stress assessment device for assessing post-insertion mechanical stress caused by a mechanical contact between a deformable object and an external device inserted into the object and positioned at a given insertion position is provided. The stress assessment device comprises:

a segmentation unit, which is configured
- to access generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object;
- to access pre-insertion object image data and post-insertion object image data, each acquired using the imaging technique and representing a three-dimensional image of the object prior to insertion of the external device and with the external device positioned at the given current insertion position, respectively;
- using the pre-insertion object image data and the generic model data, to provide segmented pre-insertion object model data which represents the object in its pre-insertion state and its spatially resolved mechanical property and comprises associated mapped pre-insertion landmark position data indicative of mapped pre-insertion positions of the secondary landmark features within the object;
- using either the post-insertion object image data and the segmented pre-insertion object model data or the post-insertion object image data and the and the generic model data, to provide insertion position data indicative of a current insertion position of the external device, and segmented post-insertion object model data which comprises associated mapped post-insertion landmark position data indicative of mapped post-insertion positions of the secondary landmark features within the object in the post-insertion state; and a stress determination unit, which is configured
- to calculate and provide, using the insertion position data, the segmented post-insertion object model data and the segmented pre-insertion object model data, post-insertion stress information data indicative of mechanical post-insertion stress exerted to at least one of the secondary landmark features by the mechanical contact between the object and the external device inserted into the object at the current insertion position.

In short, for a (post-insertion) stress assessment according to the second aspect of the invention, the segmentation unit uses the generic model data and the pre- and post-insertion image data to determine a pre-insertion object model and a post-insertion object model, which in turn form an input for the stress determination unit in determining the post-insertion stress information.

In some of the embodiments of the second aspect, the segmented post-insertion object model data is determined and provided using only the post-insertion object image data and the segmented pre-insertion object model data. In other embodiments of this aspect, the segmented post-insertion object model data is determined and provided using only the post-insertion object image data and the generic model data.

The stress assessment device of the second aspect has the advantage of allowing a determination of post-insertion stress information that is indicative of mechanical post-insertion stress exerted to at least one of the secondary landmark features by the mechanical contact between the object and the external device inserted into the object at the insertion position. As explained, such mechanical stress is caused by a displacement of the secondary landmark features due to the presence of the inserted device.

The stress assessment device of the second aspect otherwise shares the advantages and optional further features of embodiments of the stress prediction device of the first aspect of the present invention.

The described embodiments of the device of the first and second aspect can be further extended in additional preferred embodiments by a risk assessment capability. Such additional preferred embodiments comprise a risk assessment unit, which is configured to determine a trauma risk measure indicative of a risk of traumatic destruction of at least one of the secondary landmark features using the stress information data and a predetermined stress trauma criterion. Such as risk criterion is in one embodiment implemented using the determined stress information, in particular in spatially resolved form of a stress distribution, which is thus linked to locations of a deformed object mesh topology describing the post-insertion state. Similarly, the determined mapped pre-insertion landmark position data indicative of mapped pre-insertion positions of the secondary landmark features within the object, which may also be based on a statistical distribution, can be located in the registered post-insertion object-model data. An overlay of these two kinds of information, based on the object mesh topology allows to identify sections, in which a high stress level and a high likelihood for a sensitive secondary landmark feature fall together. This coincidence implies a high risk of traumatic destruction of the secondary landmark feature. In some variants, external factors are included into the function defining a trauma risk measure, such as a patient history. The overall risk function may, depending on the complexity, be learned by a machine in a supervised manner or just be a display of the stress plus likelihood.

According to a third aspect of the present invention, a method for predicting mechanical stress exerted to a deformable object due to mechanical contact between the object and an external device that is to be inserted into the object and to be positioned at a pre-determined intended insertion position is provided. The method comprises:

providing generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object;

receiving pre-insertion object image data acquired using the imaging technique and representing a three-dimensional image of the object prior to insertion of the external device;

using the pre-insertion object image data and the generic model data, providing segmented object model data which represents the object and its spatially resolved mechanical properties and comprises associated mapped landmark position data indicative of mapped landmark positions of the secondary landmark features within the object;

receiving insertion position data indicative of the pre-determined intended insertion position;

receiving device model data representing the external device;

calculating and providing, using the segmented object model data, the device model data and the intended insertion position data, predictive stress information data indicative of mechanical stress exerted to at least one of the secondary landmark features at the associated mapped landmark position by the mechanical contact between the object and the external device when inserted into the object at the intended insertion position.

The method of the third aspect of the present invention and its embodiments share the advantages of the stress prediction device of the first aspect and any of its embodiments.

According to a fourth aspect of the present invention, a stress assessment method for assessing post-insertion mechanical stress caused by a mechanical contact between a deformable object and an external device inserted into the object and positioned at a given current insertion position is provided. The method comprises:

providing generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object;

providing pre-insertion object image data and post-insertion object image data, each acquired using the imaging technique and representing a three-dimensional image of the object prior to insertion of the external device and with the external device positioned at the given current insertion position, respectively;

using the pre-insertion object image data and the generic model data, providing segmented pre-insertion object model data which represents the object in its pre-insertion state and its spatially resolved mechanical property and comprises associated mapped pre-insertion landmark position data indicative of mapped pre-insertion positions of the secondary landmark features within the object;

using either the post-insertion object image data and the segmented pre-insertion object model data or the post-insertion object image data and the and the generic model data, providing insertion position data indicative of a current insertion position of the external device, and segmented post-insertion object model data which comprises associated mapped post-insertion landmark position data indicative of mapped post-insertion positions of the secondary landmark features within the object in the post-insertion state; and calculating post-insertion stress information data indicative of mechanical post-insertion stress exerted to at least one of the secondary landmark features by the mechanical contact between the object and the external device inserted into the object at the insertion position, the calculation using the insertion position data, the segmented post-insertion object model data and the segmented pre-insertion object model data.

The method of the forth aspect of the present invention and its embodiments share the advantages and optional additional features of the stress assessment device of the second aspect and any of its embodiments.

A fifth aspect of the invention is formed by a computer program comprising executable code for executing the method of the third aspect or any of its embodiments or for executing the method of the forth aspect or any of its embodiments when executed by a processor of a computer.

It shall be understood that the stress prediction device of claim 1, the stress assessment device of claim 10, the method for predicting stress of claim 12, the method for assessing stress of claim 13, and the computer program of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

In the following, reference is made in parallel to FIG. 1, FIGS. 2A, 2B, 2C and FIG. 3.

Figure 1:
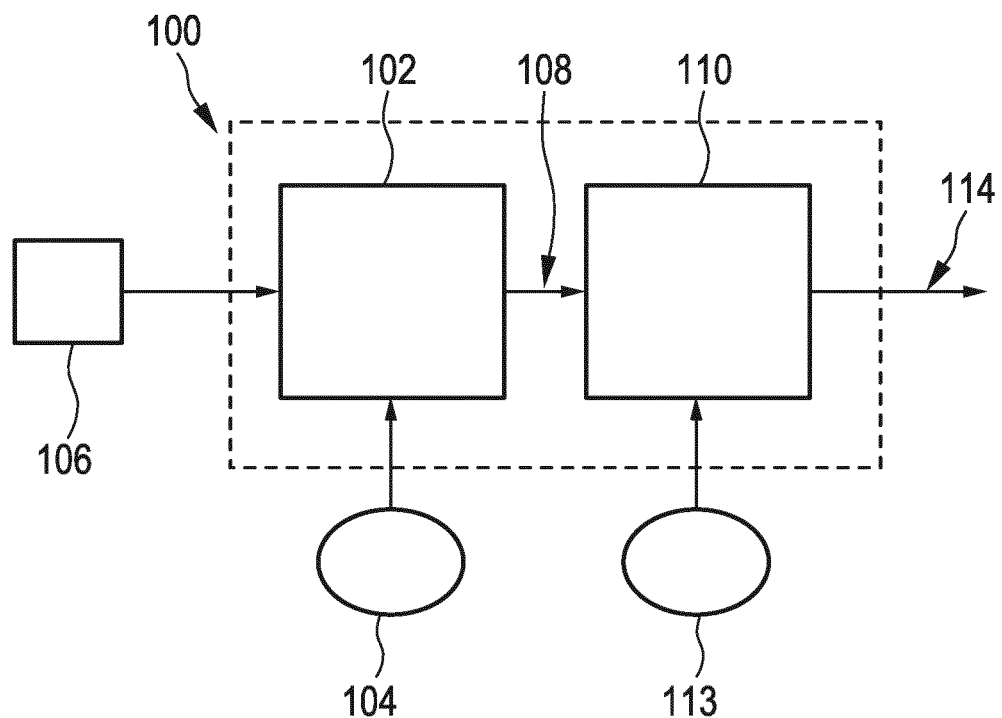
FIG. 1 shows a schematic block diagram of an embodiment of a stress prediction device for predicting mechanical stress.
Figure 2A:
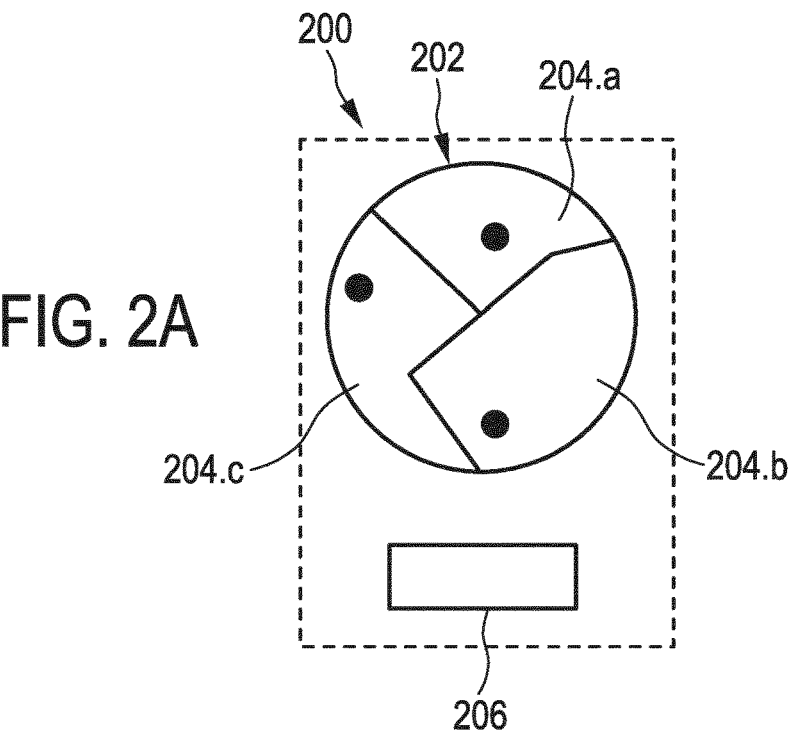
FIG. 2A shows a schematic illustration of generic model data representing a three-dimensional generic reference object.
Figure 2B:
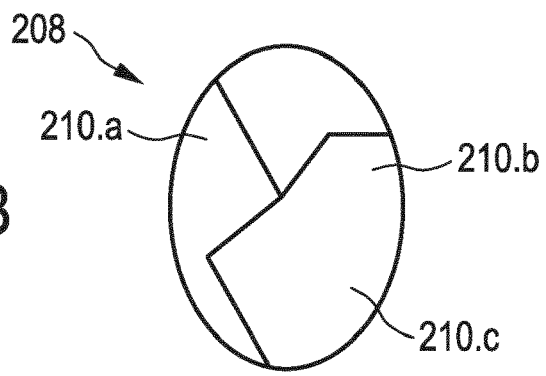
FIG. 2B shows a schematic illustration of pre-insertion object image data representing a three dimensional image of an object.
Figure 2C:
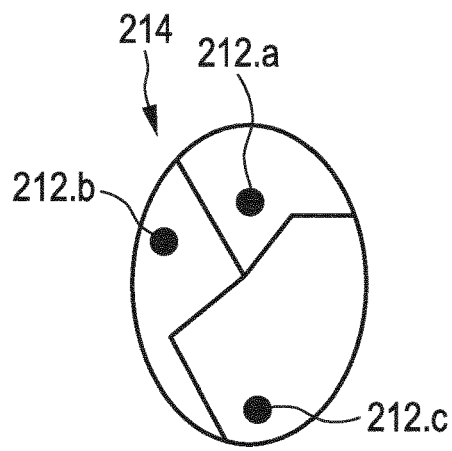
FIG. 2C shows a schematic illustration of a three dimensional object represented by segmented object model data.

FIG. 1 shows a schematic block diagram of an embodiment of a stress prediction device 100 for predicting mechanical stress expected from a mechanical contact between a deformable object 208 and an external device 302 to be inserted into the object at a predetermined intended insertion position. FIG. 2A shows a schematic illustration of generic model data 200 representing a three-dimensional generic reference object. FIG. 2B shows a schematic illustration of pre-insertion object image data 208 representing a three dimensional image of an object, and FIG. 2C shows a schematic illustration of a three dimensional object represented by segmented object model data 214.

The stress prediction device 100 comprises a segmentation unit 102 which is configured to access generic model data 104. This generic model data is also illustrated in FIG. 2A. It represents a three-dimensional generic reference object 202 having three distinguishable object regions 204.$a$, 204.$b$ and 204.$c$ that have predefined spatial positions within the three-dimensional generic reference object and are identifiable using a predefined imaging technique. The generic model data also comprises predefined secondary landmark features (represented as black circles in FIG. 2A) that have predefined second spatial positions within the three-dimensional generic reference object, which are hereinabove also called the landmark positions. These secondary landmark features are not identifiable using the imaging technique. The generic model data further comprises spatially resolved mechanical reference data 206 indicative of at least one physical quantity representing at least one mechanical property of the generic reference object. The mechanical properties can be, but are not limited to, elasticity, flexibility, resilience, compressive strength, hardness, plasticity, or ductility. Therefore, and in summary the generic model data comprises data that is related to:

a geometry or shape of the object and its object regions, a position within the object of predefined secondary landmark features (predefined landmark positions), and at least one mechanical property of the generic object. The information regarding the at least one mechanical property is spatially resolved, so that the mechanical reference data may have different values within the generic object.

The generic reference object 200 is suitably a statistical model based on a ground truth population of objects, where the geometry of the generic reference object, positions of the secondary landmark features and the spatially resolved mechanical reference data are determined by a statistical determination rule based on a plurality of objects belonging to the population.

The segmentation unit is also configured to access or receive pre-insertion object image data 106 that is acquired from the three-dimensional object using the imaging technique prior to insertion of the external device. The pre-insertion object image data represents a three-dimensional image of the object 208 having specific object regions 210.a, 210.b and 210.c corresponding to the object regions comprised by the generic model data 204.a, 204.b and 204.c. However, the object image data does not have contrast features corresponding to the secondary landmark features (black circles in FIG. 2A), because these landmark features do not result in contrast features when imaged by the imaging technique, and are therefore not identifiable using the imaging technique. The three-dimensional object belongs to a certain object type to which the generic reference object also belongs, although they do not necessarily have an exact same shape, size or geometry (as an example, the generic reference object 202 has a spherical shape, whereas the three dimensional image 208 of the object has an ovoid-like shape).

The segmentation unit 102 is further configured to use the pre-insertion object image data 106 and the generic model data 104 in order to provide segmented object model data 214 which represents the three-dimensional object and its spatially resolved mechanical property and comprises associated mapped landmark position data indicative of mapped landmark positions 212.a, 212.b and 212.c. of the secondary landmark features within the object. Suitable mechanical properties are for instance elasticity, flexibility, resilience, compressive strength, hardness, plasticity or ductility.

The segmentation unit 102 also provides segmented object model data 108 to a stress determination unit 110. The segmented object model data 108 thus represents the three-dimensional object 214 and includes mapped landmark position data that is relevant to the mapped position of the secondary landmark features that are not identifiable by the imaging technique.

As stated above, the stress prediction device 100 comprises a stress determination unit 110 that is configured to additionally receive the receive insertion position data 112 indicative of the pre-determined intended insertion position and device model data 113, which represents the external device for use in addition to the segmented object model data 108 for calculating predictive stress information indicative of mechanical stress exerted to at least one of the secondary landmark features at the associated mapped landmark position due to mechanical contact between the object and the external device when inserted into the object at the intended insertion position.

The mechanical stress is suitably determined in the form of a three-dimensional distribution of stress in the object. As such, the stress determination unit 110 also allows calculating mechanical stress at the mapped positions (212.a-c), which are the expected positions of the secondary landmark features in the object. The calculation takes into account the mechanical contact interaction between the object and the external device when inserted into the object at the given insertion position. The stress determination unit 110 outputs predictive stress information data 114 that is indicative of the determined mechanical stress at the mapped positions.

Figure 3:
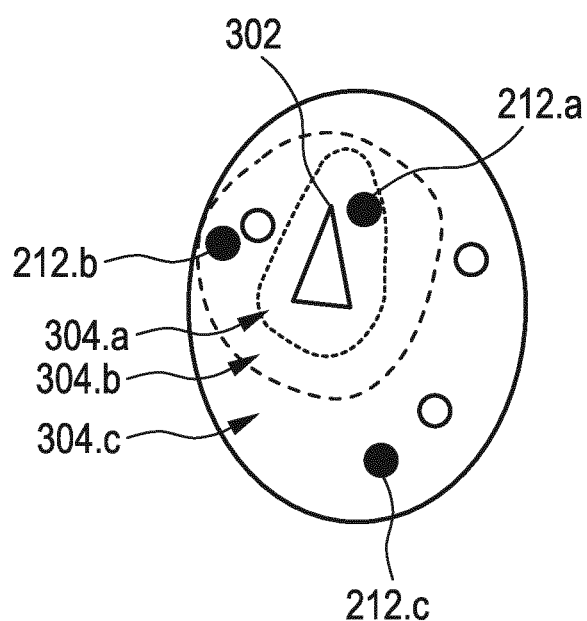
FIG. 3 illustrates an interaction between the object and the external device.

An interaction due to mechanical contact between the object and the external device is shown in FIG. 3. The external device 302 is to be inserted at the position shown in the figure, and the stress determination unit calculates the mechanical stress expected from the insertion of the external device at that particular insertion position. In this particular case, the three different areas regions 304.a-c at different distance intervals from the insertion position are subject to decreasing values of stress with increasing distance. The mapped landmark position 212.a, located within the region 304.a, is under a higher stress level than the mapped position 212.b located in region 304.b, which is in turn under a higher stress level than mapped position 212.c, located in region 304.c. The actual geometries of the regions 304.a-c depend on the geometry of the object and of the external device 302, on its respective mechanical properties and on the insertion position.

In one particularly advantageous example, the object under investigation is a heart. The segmentation unit has access to generic model data that represents a three dimensional reference heart. The generic model data pertains to a multi-compartment triangulated mesh made of V vertices connected in T triangles. The mesh geometry arises from the interconnection of elementary geometric entities like ellipsoids for the heart chambers and cylinders for the great vessels In one particular example the resulting triangular mesh comprises V=7286 vertices combined in T=14771 triangles with complex junctions connecting 3 or more surfaces. Edge lengths range between 2.5 and 5.0 mm. Seven anatomical regions are enclosed by the mesh, namely both ventricles and both atria, the myocardium around the LV as well as the trunks of the aorta, the pulmonary artery and the pulmonary veins. The generic reference heart also includes predefined secondary landmark features that are not identifiable using the imaging technique. In this example, and using CT as the imaging technique, an example of the secondary landmark features are the features of the conductive system including at least one of the AV node, the His bundle and a fraction of the left or right bundle branch. The conductive system or electrical conduction system of the heart allows the electrical impulse generated by the sinoatrial node to be propagated to, and stimulate, the myocardium or cardiac muscle. Although the conductive system cannot be distinguished from other tissues directly by CT imaging, the generic model data of the reference heart includes information regarding the landmark position of the secondary landmark features in relation to the mesh that has been previously obtained by other means known to those skilled in the art. This is sometimes done by applying other imaging techniques that enable the identification of the positions of the secondary landmarks on one or more reference objects. In other cases, the position of the secondary landmarks belonging to the conductive system can be determined for a number of reference hearts via EP-catheter applications.

The segmentation unit performs a model-based segmentation algorithm, which as such is known in the art, and provides segmented object model data that represents the three-dimensional heart imaged. The segmented object model data may thus comprise mesh data defining a shape of the heart under investigation. The segmented object model data also comprises registered spatially resolved mechanical data indicative of the at least one physical quantity representing at least one mechanical property of the heart.

The segmentation unit further maps the positions of the secondary landmark features. In particular, features of the conductive system that are not identifiable in the object (heart) image data are allocated to mapped landmark positions within the segmented object model data of the individual heart under investigation.

The heart model-based segmentation of the heart based on CT-image data includes in some embodiments the following steps:

a) Heart localization: the position of the heart is found in the image using a 3-D Generalized Hough Transform (GHT). The heart model is then translated, scaled and, where applicable, rotated according to a maximum value of an accumulator array;

b) Parametric Adaptation (1)—Similarity Transformation: at this stage, the model is still far from the optimal cardiac boundaries. In particular, the global pose has yet to be refined (up to now the model has not been rotated). To correct for misalignments in translation, rotation and scaling a single similarity transformation is used for the whole model. For this step, a parameter set for boundary detection with larger capture range may be used;

c) Parametric Adaptation (2)—Piecewise Affine Transformation: the constraints on the deformation are then relaxed by allowing the model to deform with respect to the piecewise affine transformation. This second parametric adaptation will globally resize and deform each part of the model individually to the actual subject's anatomy and phase of the cardiac cycle;

d) Deformable Adaptation: Finally, accurate adaptation of the model to the organ boundaries is performed using a deformable framework;

The stress determination unit of this stress assessment device receives the segmented object model data, which includes information pertaining to:

the geometry of the imaged heart, the mapped landmark position of the secondary landmark features that are not identifiable on the object image data acquired by the imaging technique, and at least one physical quantity representing at least one mechanical property of the object, in the form of registered spatially resolved mechanical data.

It also receives device model data which represents the external device and comprises device mechanical data indicative of the at least one physical quantity representing the at least one mechanical property of the external device. This device model data may also be provided in the form of mesh data carrying information pertaining to the geometry of the device (e.g. shape, size, diameter) as well as device-specific mechanical data indicative of at least the same physical quantity representing the mechanical property in this case of the external device.

The stress determination unit calculates predictive stress information indicative of spatially resolved mechanical stress exerted to at least one of the secondary landmark features at the associated mapped landmark position due to mechanical contact between the object and the external device when inserted into the object at the intended insertion position. To this end, the stress determination unit is configured to use the segmented object model data, the device model data and the intended insertion position data. This calculation is suitably performed using a finite element method. A deformation of the object due to mechanical stress corresponds to a displacement of mesh points, triangles or vertices comprised in the segmented object model data.

By predicting a stress distribution expected from the interaction between the heart and the external device, especially at or near the mapped landmark positions that pertain to the conductive system, a more accurate prediction of possible complications due to traumatic destruction of parts of the conductive system induced by the presence of the external device at the desired insertion position is provided. Higher stress in the vicinity of the structures of the conductive system is linked to higher risk of conductive dysfunction caused by the insertion of the external device.

Figure 4:
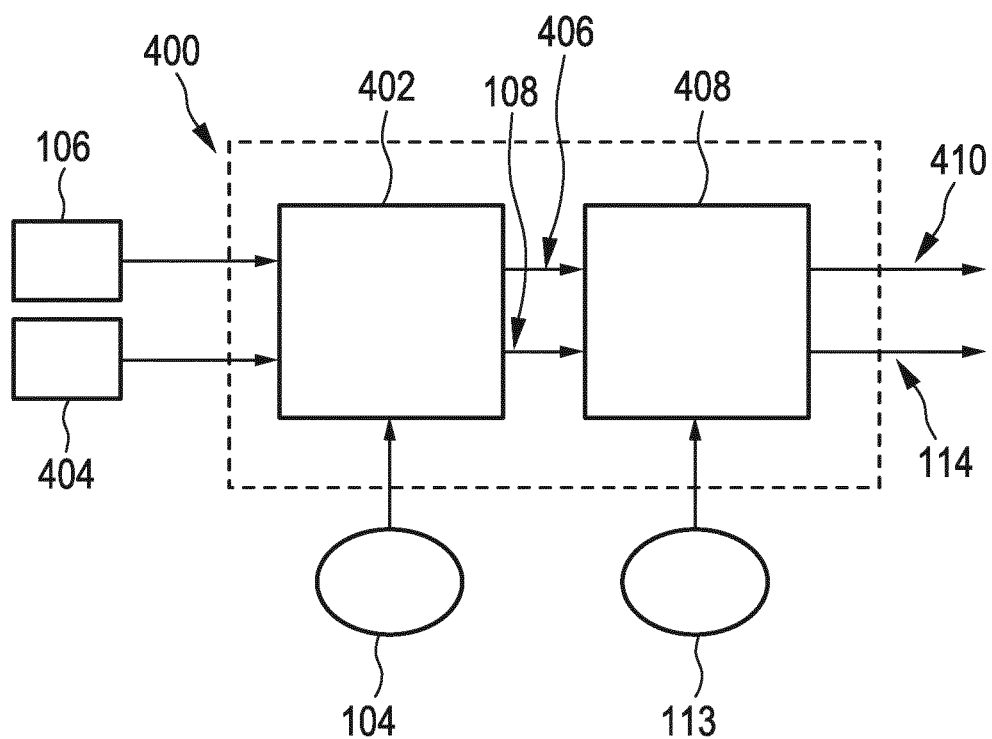
FIG. 4 shows a schematic block diagram of an embodiment of a stress assessment device for assessing mechanical stress.

FIG. 4 shows an embodiment of a stress assessment device 400 for assessing post-insertion mechanical stress caused by a mechanical contact interaction between a deformable object and an external device inserted into the object at a given current insertion position. The stress assessment device comprises a stress prediction device in which the segmentation unit 402 is further configured to receive post-insertion object image data 404 acquired using the imaging technique, and representing a the three-dimensional image of the object with the external device positioned at a given current insertion position. Furthermore, the segmentation unit 402 using the post-insertion object image data and the segmented pre-insertion image data, also provides segmented post-insertion object model data 406 which comprises associated mapped post-insertion landmark position data indicative of mapped post-insertion positions of the secondary landmark features within the object in the post-insertion state.

The segmented post-insertion object model data 406 is received together with the segmented pre-insertion object model data 108 by the stress determination unit 408, which is further configured to calculate post-insertion stress information indicative of mechanical post-insertion stress exerted to at least one of the secondary landmark features by the mechanical contact between the object and the external device inserted into the object at the current insertion position. The stress determination unit is also configured to output the post insertion stress information data 410 indicative of the mechanical stress calculated this way.

The predicted stress information data 114 thus pertains to predicted mechanical stress calculated based, among other things, on device model data representing a device that is to be inserted at a predetermined intended position. On the other hand, the post-insertion stress information data 410 pertains to assessed mechanical stress calculated based on the post-insertion object image data, i.e. once the device has been inserted in the object at the current position. This stress assessment device is therefore advantageously configured to provide the necessary information to compare the expected stress from a device to be inserted with the exerted stress by a device already inserted into the object. This enables a feedback loop to improve long-term prediction capabilities of the stress assessment device 408.

In the cases where the stress assessment device is used to predict and assess the mechanical stress expected and caused by a stent (the external device) placed in the vicinity of an aortic valve of a heart (the object), the evaluation of the predicted stress, in the form of stress information data 114 can be used to assist a planning process of the insertion of the device (e.g. a pericardial valve attached to a metal stent), especially in terms of insertion location, geometry and mechanical properties of the device. Additionally, the stress assessment device can be also used to compare the mechanical stress predicted from the device model data, with the actual stress that a device characterized by the device model data and inserted into the current insertion position is currently causing on the object.

Mechanical stress exerted to the conductive system by a device inserted in a heart is a cause of conductive dysfunction, which is one of the major complications of transcatheter aortic valve implantation (TAVI). An a priori estimation or prediction of the expected stress is aimed to assist in selecting the optimal device (in terms of size, material, design etc.) and the insertion position within the heart. Additionally, by assessing the stress the device currently inserted in the heart is exerting on the conductive system, the risk of possible post-insertion complications can be evaluated.

Figure 5:
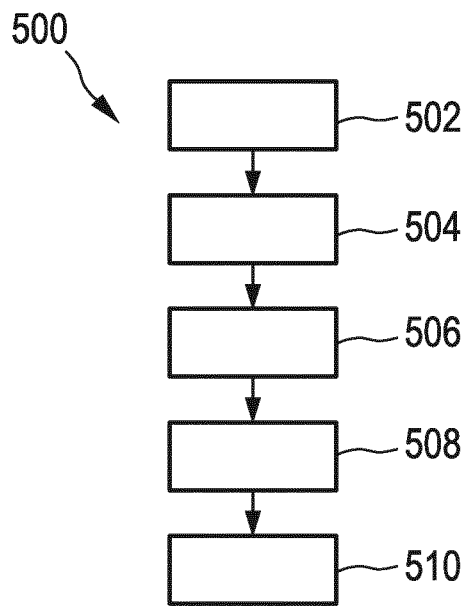
FIG. 5 shows a flow diagram of an embodiment of a method for predicting mechanical stress.

FIG. 5 shows an embodiment 500 of a method for predicting mechanical stress expected from a mechanical contact interaction between a deformable object and an external device to be inserted into the object at a predetermined intended insertion position. The method comprises providing, in step 502, generic model data, which represents a three-dimensional generic reference comprising predefined secondary landmark features at predefined landmark positions, which are not identifiable using a predefined imaging technique, and which comprises spatially resolved mechanical reference data representing at least one mechanical property of the generic reference object. In a step 504, the method comprises receiving pre-insertion object image data acquired from the three-dimensional object of the object type using the imaging technique. The method then comprises providing, in step 506, segmented object model data which represents the object and its spatially resolved mechanical property and comprises associated mapped landmark position data indicative of mapped landmark positions of the secondary landmark features within the object. This step is performed by using the pre-insertion object image data and the generic model data. In a step 508, the method then receives insertion position data indicative of the predetermined intended insertion position and device model data representing the external device, and calculates using the segmented object model data, the device model data, and the intended insertion position data, predictive stress information data indicative of mechanical stress exerted to at least one of the secondary landmark features at the associated mapped landmark position by the mechanical contact between the object and the external device when inserted into the object at the intended insertion position. Finally, in a step 510, the method provides the predictive stress information data calculated in step 508.

Figure 6:
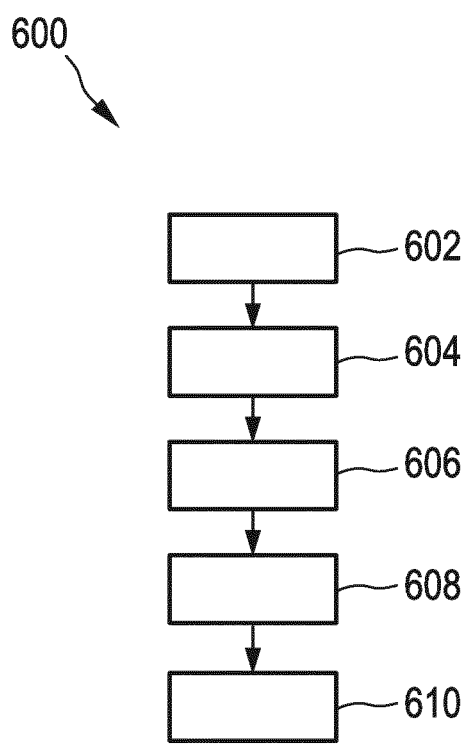
FIG. 6 shows a flow diagram of an embodiment of a method for assessing mechanical stress.

FIG. 6 shows an embodiment of a method 600 for assessing post-insertion mechanical stress caused by a mechanical contact between a deformable object and an external device inserted into the object and positioned at a given current insertion position. The method 600 comprises, in a step 602, providing generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object. In a step 604, the method provides pre-insertion object image data and post-insertion object image data, each acquired using the imaging technique and representing a three-dimensional image of the object prior to insertion of the external device and with the external device positioned at the given current insertion position, respectively. Furthermore, the method provides in a step 606, and using the pre-insertion object image data and the generic model data, segmented pre-insertion object model data which represents the object in its pre-insertion state and its spatially resolved mechanical property, and which comprises associated mapped pre-insertion landmark position data indicative of mapped pre-insertion positions of the secondary landmark features within the object as well as mapped spatially resolved mechanical data representing the mechanical property of the object.

The method also provides, in a step 608, and using either the post-insertion object image data and the segmented pre-insertion object model data or the post-insertion object image data and the generic model data, insertion position data indicative of a current insertion position of the external device, and segmented post-insertion object model data which comprises associated mapped post-insertion landmark position data indicative of mapped post-insertion positions of the secondary landmark features within the object in the post-insertion state. Finally, the method calculates, in a step 610, post-insertion stress information data indicative of mechanical post-insertion stress exerted to at least one of the secondary landmark features by the mechanical contact between the object and the external device inserted into the object at the insertion position, the calculation using the segmented post-insertion object model data, and the segmented pre-insertion object model data.

In summary, a stress prediction device for predicting mechanical stress exerted to a deformable object due contact between the object and an external device that is to be inserted into the object at an intended insertion position comprises a segmentation unit configured to access generic model data representing a generic reference object that comprises predefined secondary landmark features at predefined landmark positions, which are not identifiable using a predefined imaging technique, and pre-insertion object image data acquired using the imaging technique. It provides segmented object model data which comprises associated mapped landmark position data indicative of mapped landmark positions of the secondary landmark features. A stress determination unit determines and provides predictive stress information indicative of mechanical stress exerted to at least one of the secondary landmark features at the associated mapped landmark position due to mechanical contact between the object and the external device.

Other variations to the disclosed embodiments can be understood and effected by those skilled in the art in practicing the claimed invention, from a study of the drawings, the disclosure, and the appended claims. Other application cases of the embodiments described herein are found in orthopedics.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A stress prediction device for predicting mechanical stress exerted to a deformable object due to mechanical contact between the object and an external device that is to be inserted into the object and to be positioned at a predetermined intended insertion position, comprising:

a segmentation unit, which is configured
to access generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object, and to access pre-insertion object image data acquired using the imaging technique and representing a three-dimensional image of the object prior to insertion of the external device;
using the pre-insertion object image data and the generic model data, to provide segmented object model data which represents the object and its spatially resolved mechanical property and comprises associated mapped landmark position data indicative of mapped landmark positions of the secondary landmark features within the object; and comprising:
a stress determination unit, which is configured
to receive insertion position data indicative of the intended insertion position, and device model data, which represents the external device, and
to calculate and provide, using the segmented object model data, the device model data and the intended insertion position data predictive stress information indicative of mechanical stress exerted to at least one of the secondary landmark features at the associated mapped landmark position due to mechanical contact between the object and the external device when inserted into the object at the intended insertion position.

2. The stress prediction device of claim 1, wherein the pre-insertion object image data is computed tomography data acquired by a computed tomography imaging technique.

3. The stress prediction device of claim 2, wherein the device model data represents a balloon-inflatable stent as the external device, and wherein the stress determination unit is configured to calculate the mechanical stress using a predetermined balloon force value indicative of a radial force applied by the balloon-inflatable stent in an inflated state to radially surrounding tissue of the object at the insertion position.

4. The stress prediction device of claim 2, wherein the device model data represents a self-expandable stent as the external device, and wherein the stress determination unit is configured to calculate the mechanical stress using a predetermined expansion force value indicative of a radial force applied by the self-expandable stent in an expanded state to radially surrounding tissue of the object at the insertion position.

5. The stress prediction device of claim 1, wherein the generic model data represents a three-dimensional generic reference heart and the object image data is heart image data acquired from a heart of a living being.

6. The stress prediction device of claim 5, wherein the secondary landmark features comprise at least one part of a heart-conductive system including at least one of an AV node, a His bundle and a fraction of a left or right bundle branch, which are not identifiable using the computed tomography imaging technique.

7. The stress prediction device of claim 1, wherein the generic model data, the segmented object model data and the device model data comprises respective mesh data defining a shape of the generic reference object, the object and the external device, respectively, and wherein the stress determination unit is configured to calculate the mechanical stress using a finite element method.

8. The stress prediction device of claim 1, wherein
the generic model data represents a three-dimensional generic reference object that includes primary landmark features associated with pre-determined primary landmark positions and identifiable in the object image data using the predefined imaging technique, and wherein
the segmentation unit is configured to determine the mapped landmark positions using the primary landmark positions.

9. The stress prediction device according to claim 1, wherein
the segmentation unit is additionally configured to receive post-insertion object image data acquired, using the imaging technique, from the three-dimensional object with the external device positioned at a given current insertion position;
using either the post-insertion object image data and the segmented pre-insertion object model data or the post-insertion object image data and the generic model data, to provide insertion position data indicative of a current insertion position of the external device, and segmented post-insertion object model data which comprises associated mapped post-insertion landmark position data indicative of mapped post-insertion positions of the secondary landmark features within the object in the post-insertion state;
and wherein the stress determination unit is additionally configured
to calculate and provide, using the insertion position data, the segmented pre-insertion object model data and the segmented post-insertion object model data, post-insertion stress information data indicative of mechanical post-insertion stress exerted to at least one of the second landmark features by the mechanical contact between the object and the external device inserted into the object at the current insertion position.

10. The stress prediction device according to claim 1, further comprising a risk assessment unit, which is configured to determine a trauma risk measure indicative of a risk of traumatic destruction of at least one of the secondary landmark features using the stress information data and a predetermined stress trauma criterion.

11. A stress assessment device for assessing post-insertion mechanical stress caused by a mechanical contact between a deformable object and an external device inserted into the object and positioned at a given current insertion position, comprising:
a segmentation unit, which is configured
to access generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object;
to access pre-insertion object image data and post-insertion object image data, each acquired using the imaging technique and representing a three-dimensional image of the object prior to insertion of the external device and with the external device positioned at the given current insertion position, respectively;

using the pre-insertion object image data and the generic model data, to provide segmented pre-insertion object model data which represents the object in its pre-insertion state and its spatially resolved mechanical property and comprises associated mapped pre-insertion landmark position data indicative of mapped pre-insertion positions of the secondary landmark features within the object;

using either the post-insertion object image data and the segmented pre-insertion object model data or the post-insertion object image data and the generic model data, to provide insertion position data indicative of a current insertion position of the external device, and segmented post-insertion object model data which comprises associated mapped post-insertion landmark position data indicative of mapped post-insertion positions of the secondary landmark features within the object in the post-insertion state; and a stress determination unit, which is configured
to calculate and provide, using the insertion position data, the segmented post-insertion object model data and the segmented pre-insertion object model data, post-insertion stress information data indicative of mechanical post-insertion stress exerted to at least one of the secondary landmark features by the mechanical contact between the object and the external device inserted into the object at the current insertion position.

12. A method for predicting mechanical stress exerted to a deformable object due to mechanical contact between the object and an external device that is to be inserted into the object and to be positioned at a pre-determined intended insertion position, the method comprising:

providing generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object;

receiving pre-insertion object image data acquired using the imaging technique and representing a three-dimensional image of the object prior to insertion of the external device;

using the pre-insertion object image data and the generic model data, providing segmented object model data which represents the object and its spatially resolved mechanical property and comprises associated mapped landmark position data indicative of mapped landmark positions of the secondary landmark features within the object;

receiving insertion position data indicative of the pre-determined intended insertion position;

receiving device model data representing the external device;

calculating and providing, using the segmented object model data, the device model data and the intended insertion position data, predictive stress information data indicative of mechanical stress exerted to at least one of the secondary landmark features at the associated mapped landmark position by the mechanical contact between the object and the external device when inserted into the object at the intended insertion position.

13. A non-transitory computer readable medium comprising executable code for executing the method of claim 12 when executed by a processor of a computer.

14. A method for assessing post-insertion mechanical stress caused by a mechanical contact between a deformable object and an external device inserted into the object and positioned at a given current insertion position, comprising:

providing generic model data, which represents a three-dimensional generic reference object comprising predefined secondary landmark features at predefined landmark positions, which are not identifiable using a predefined imaging technique, and which comprises spatially resolved mechanical reference data representing at least one mechanical property of the generic reference object;

providing pre-insertion object image data and post-insertion object image data, each acquired using the imaging technique and representing a three-dimensional image of the object prior to insertion of the external device and with the external device positioned at the given current insertion position, respectively;

using the pre-insertion object image data and the generic model data, providing segmented pre-insertion object model data which represents the object in its pre-insertion state and its spatially resolved mechanical property, and comprises associated mapped pre-insertion landmark position data indicative of mapped pre-insertion positions of the secondary landmark features within the object as;

using either the post-insertion object image data and the segmented pre-insertion object model data or the post-insertion object image data and the generic model data, providing insertion position data indicative of a current insertion position of the external device, and segmented post-insertion object model data which comprises associated mapped post-insertion landmark position data indicative of mapped post-insertion positions of the secondary landmark features within the object in the post-insertion state; and calculating post-insertion stress information data indicative of mechanical post-insertion stress exerted to at least one of the secondary landmark features by the mechanical contact between the object and the external device inserted into the object at the insertion position, the calculation using the insertion position data, the segmented post-insertion object model data, and the segmented pre-insertion object model data.

* * * * *